(12) United States Patent
Huang

(10) Patent No.: US 10,004,503 B2
(45) Date of Patent: Jun. 26, 2018

(54) STAPLES PUSH UNIT FOR TACKERS

(71) Applicant: Tsung-Wen Huang, Chang Hua County (TW)

(72) Inventor: Tsung-Wen Huang, Chang Hua County (TW)

( * ) Notice: Subject to any disclaimer, the term of this patent is extended or adjusted under 35 U.S.C. 154(b) by 451 days.

(21) Appl. No.: 14/884,867

(22) Filed: Oct. 16, 2015

(65) Prior Publication Data

US 2017/0105734 A1     Apr. 20, 2017

(51) Int. Cl.
*A61B 17/10*     (2006.01)
*A61B 17/068*    (2006.01)

(52) U.S. Cl.
CPC .......... *A61B 17/105* (2013.01); *A61B 17/068* (2013.01)

(58) Field of Classification Search
CPC . A61B 17/068; A61B 17/105; A61B 17/0682; B25C 5/15; B25C 5/11
USPC ......................................... 227/134, 8, 177.1
See application file for complete search history.

(56) References Cited

U.S. PATENT DOCUMENTS 3,766,455 A * 10/1973 Zakrewsky ............... B25C 1/06
                                                       227/131
2015/0314433 A1* 11/2015 Fleischer .................. B25C 5/15
                                                       227/132

* cited by examiner

*Primary Examiner* — Robert Long
*Assistant Examiner* — Xavier A Madison
(74) *Attorney, Agent, or Firm* — Bacon & Thomas, PLLC

(57) ABSTRACT

A staples push unit of a tacker includes a guide plate located at a staple outlet of the tacker. A motor is located in the tacker and has an output shaft to which a driving gear is connected. A slide and a push plate connected to the slide are movably located in a slot in the tacker. A rack is formed at one side of the slide and engaged with the teeth of the driving gear. A spring board has one end engaged with one end of the slide. When activating the motor, the driving gear drives the rack to move the slide, and the spring board is bent. When the teeth of the driving gear are disengaged from the rack, the spring board bounces back and drives the slide and the push plate to eject a staple. The push plate is guided by the guide plate.

7 Claims, 10 Drawing Sheets

STAPLES PUSH UNIT FOR TACKERS

BACKGROUND OF THE INVENTION

1. Fields of the Invention

The present invention relates to a tacker, and more particularly, to a staple push unit of a power tacker.

2. Descriptions of Related Art

The conventional tacker known to the applicant is disclosed in FIG. 8, and comprises a motor 70 with an output shaft 72, and a cam 73 is connected to the output shaft 72. A staple push unit is located in the tacker and has a push plate 74, a switch plate 75 and a spring 77, wherein the spring 77 is located in casing 76, and the switch plate 75 is located beside the spring 77. The switch plate 75 is driven by the cam 73 so as to simultaneously activate the switch plate 75 and the spring 77. The push plate 74 is located above the switch plate 75. The user pulls the trigger 71 to activate the motor 70 and the output shaft 72 which rotates the cam 73. The cam 73 pushes the switch plate 75 and compress the spring 77 to store energy. As shown in FIG. 9, when the cam 73 rotates over the switch plate 75, the switch plate 75 is not pushed by the cam 73, so that the spring 77 is released and the energy of the spring 77 pushes the push plate 74 to eject the staple 78 out and into an object as shown in FIG. 10.

However, the cam 73 is cylindrical part with a smooth outside, and the spring 77 applies a significant force to the switch plate 75, so that the friction between the cam 73 and the switch plate 75 can easily wear out the both of the cam 73 and the switch plate 75. This may affects the precision of the ejection of the staples.

The present invention intends to provide a staples push unit of a power tacker to eliminate the shortcomings mentioned above.

SUMMARY OF THE INVENTION

The present invention relates to a staples push unit of a tacker and comprises a magazine connected to the front end of the tacker for receiving staples therein. A slot is defined in the tacker, and a guide plate is located in the tacker and located at a staple outlet of the tacker. A motor is located in the tacker and has an output shaft. A driving gear is connected to the output shaft and has teeth defined in the outer periphery thereof. A trigger is electrically connected to the motor. A push unit is located in the slot and has a slide a push plate which is connected to the first end of the slide. The slide has a notch defined in the second end thereof. The slide has a rack formed at one side thereof. The rack is engaged with the teeth of the driving gear. The push plate is located within the guide plate and guided by the guide plate. A spring board is located in the tacker and has an end engaged with the notch of the slide.

When pulling the trigger, the driving gear drives the rack to move the slide away from the staple outlet of the tacker, and the spring board is bent with movement of the slide. When the teeth of the driving gear are disengaged from the rack. The spring board bounces back and drives the slide and the push plate toward the staple outlet of the tacker to eject a staple out from the staple outlet.

Preferably, the guide plate is located above an opening of the magazine.

Preferably, the guide plate has two sidewalls between which a guide path is defined. The push plate is movably located in the guide path.

Preferably, the rack on the slide is a straight rack and movable in the slot.

Preferably, the teeth are defined in a portion of the outer periphery of the driving gear.

Preferably, a spring is located in the trigger.

Preferably, the push plate is connected to the slide by a pin.

The primary object of the present invention is to provide a staple push unit of a tacker, wherein the teeth of the driving gear directly drive the rack of the slide to activate the push plate to eject the staples, the transmission between the teeth of the driving gear and the rack of the slide is stable and precise.

Another object of the present invention is to provide a push unit of a tacker, wherein the spring board is directly engaged with the notch of the slide so when the teeth of the driving gear are disengaged from the rack of the slide, the spring board directly pushes the slide and the push plate to precisely eject the staples.

The present invention will become more obvious from the following description when taken in connection with the accompanying drawings which show, for purposes of illustration only, a preferred embodiment in accordance with the present invention.

DETAILED DESCRIPTION OF THE PREFERRED EMBODIMENT

Figure 1:
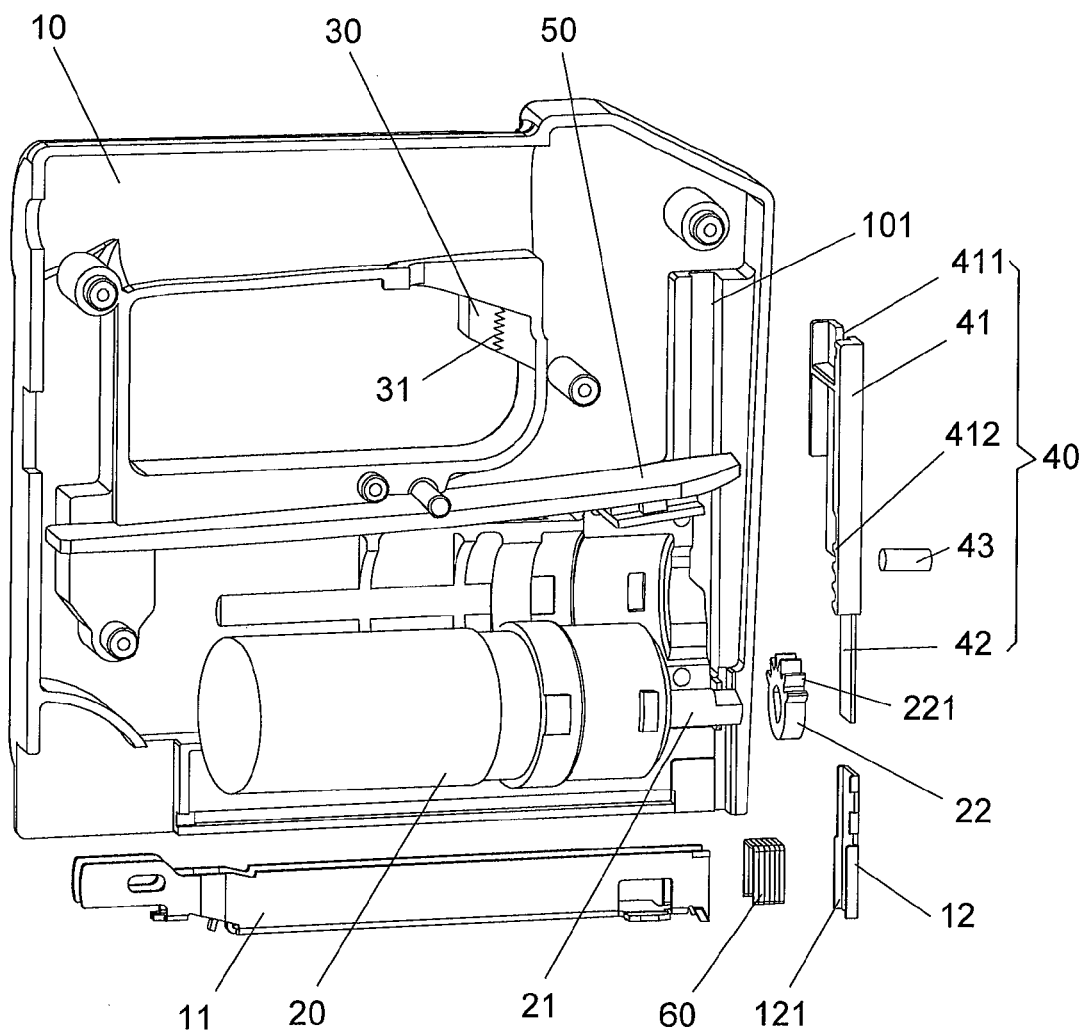
FIG. 1 is an exploded view of the push unit of the present invention and the tacker.
Figure 2:
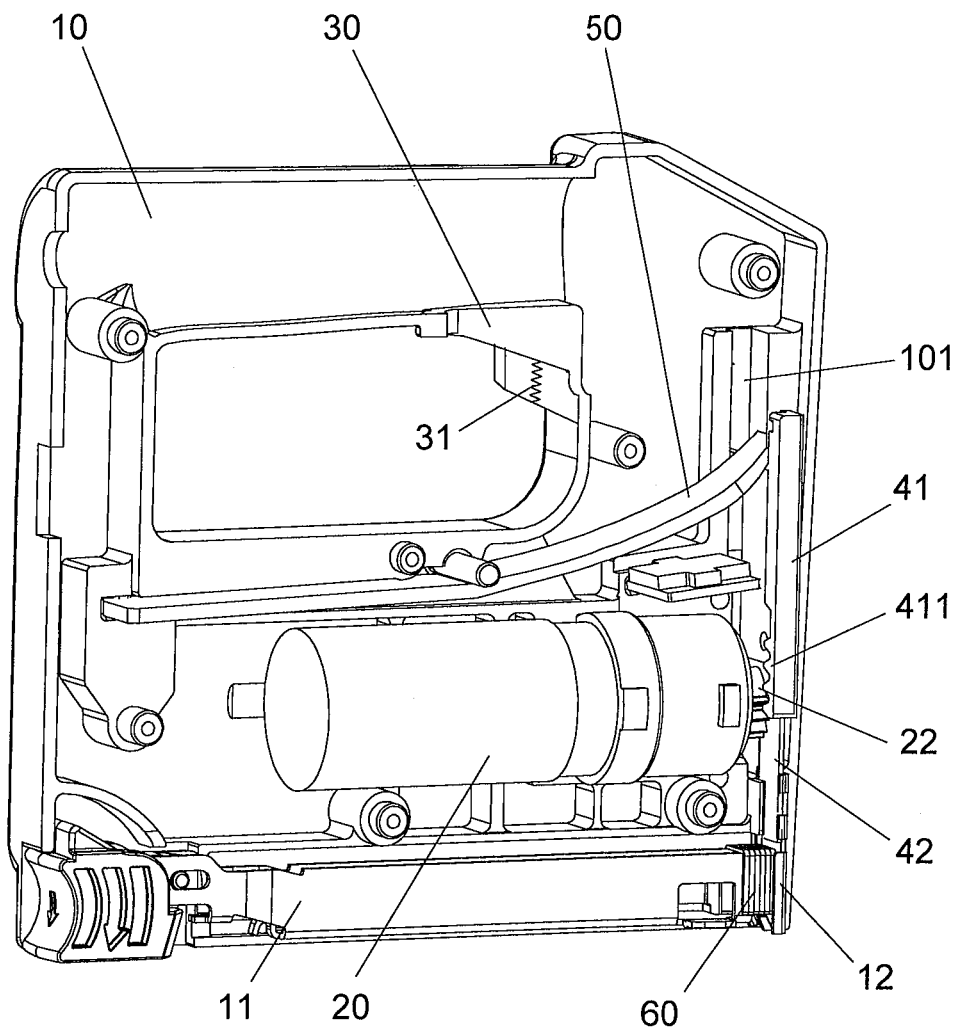
FIG. 2 shows that the push unit of the present invention is installed in the tacker.
Figure 3:
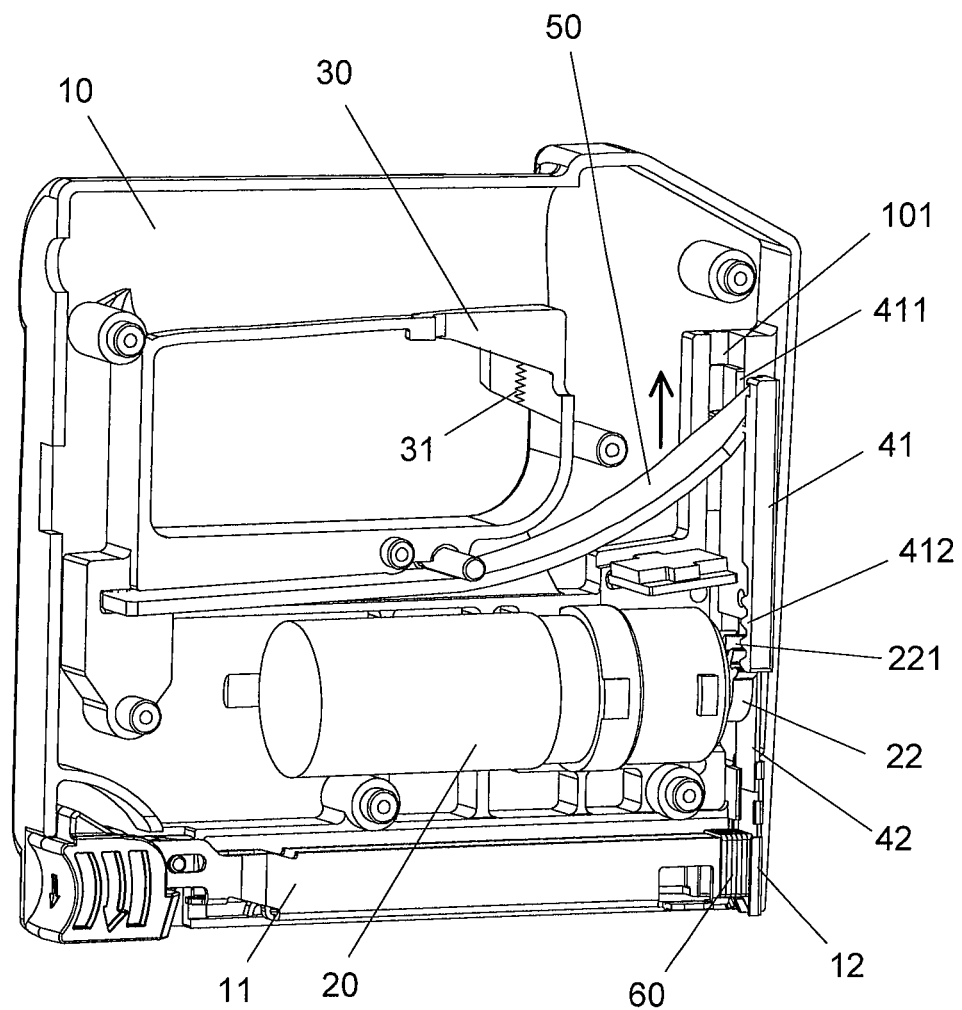
FIG. 3 shows that the slide is moved by the driving gear and the spring board is bent.
Figure 4:
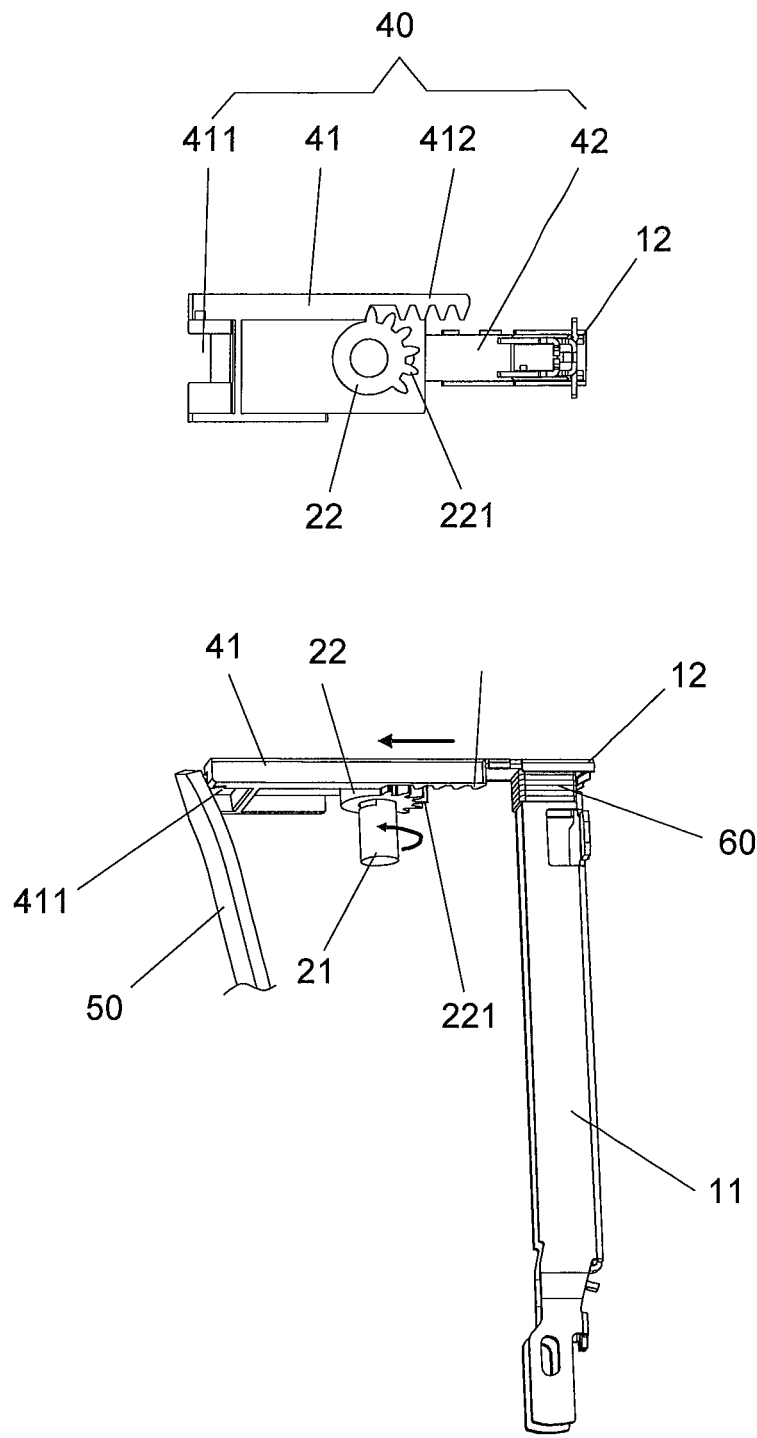
FIGS. 4 to 5 show that the driving gear is rotated to drive the rack and the slide toward left.

Referring to FIGS. 1 to 7, the staples push unit of a tacker 10 of the present invention comprises a magazine 11 connected to the front end of the tacker 10, the magazine 11 has an opening at the top thereof. Staples are receive staples 60 in the magazine 11 and pushed by a pushing mechanism in the magazine 11 toward the opening. A slot 101 is defined in the tacker 10 and perpendicular to the magazine 11. A guide plate 12 is located in the tacker 10 and located at the staple outlet of the tacker 10 and above the opening of the magazine 11.

A motor 20 is located in the tacker 10 and has an output shaft 21. A driving gear 22 is connected to the output shaft 21 and has teeth 221 defined in a portion of the outer periphery thereof. A trigger 30 is electrically connected to the motor 20 and a spring 31 is located in the trigger 30.

A push unit 40 is located in the slot 101 and has a slide 41 and a push plate 42 which is connected to the first end of the slide 41 by a pin 43. The slide 41 has a notch 411 defined in the second end thereof. A rack 412 is formed at one side thereof and the rack 412 is a straight rack which is movable in the slot 101. The rack 412 is engaged with the teeth 221 of the driving gear 22. The push plate 42 is located within the guide plate 12 and guided by the guide plate 12. The guide plate 12 has two sidewalls between which a guide path 121 is defined. The push plate 42 is movably located in the guide path 121.

A spring board 50 has one end fixed to the inside of the tacker 10 and the other end of the spring board 50 is engaged with the notch 411 of the slide 41.

Figure 5:
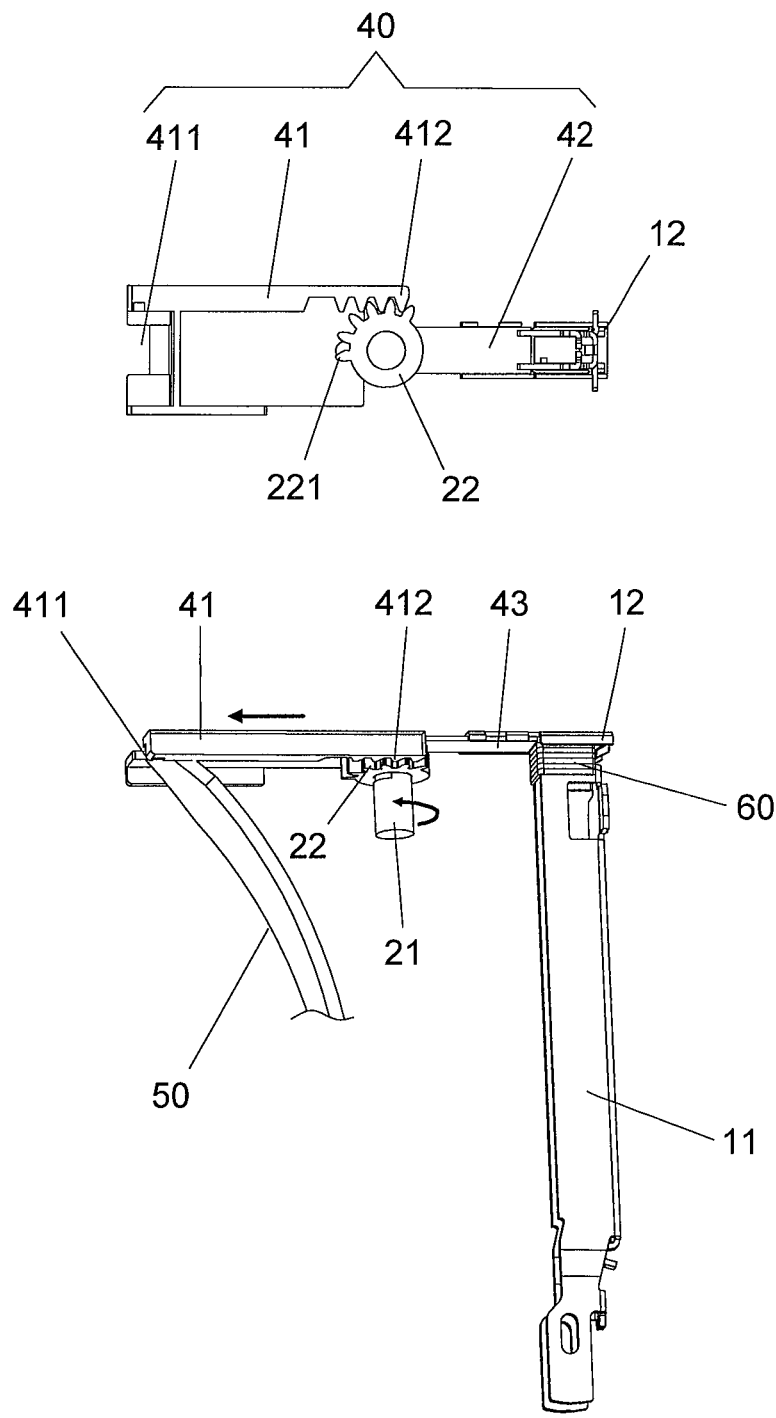
Figure 6:
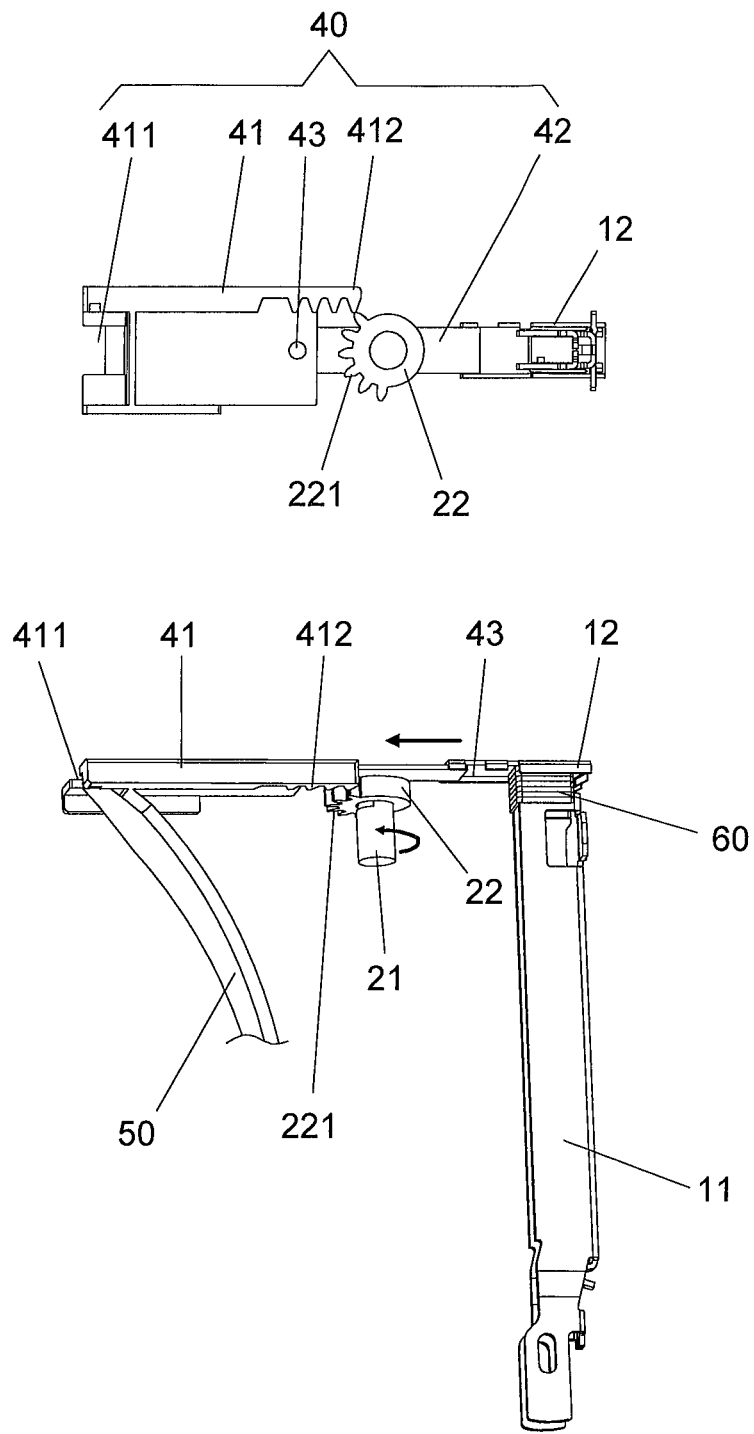
FIG. 6 shows that the teeth of the driving gear are about to be disengaged from the rack.
Figure 7:
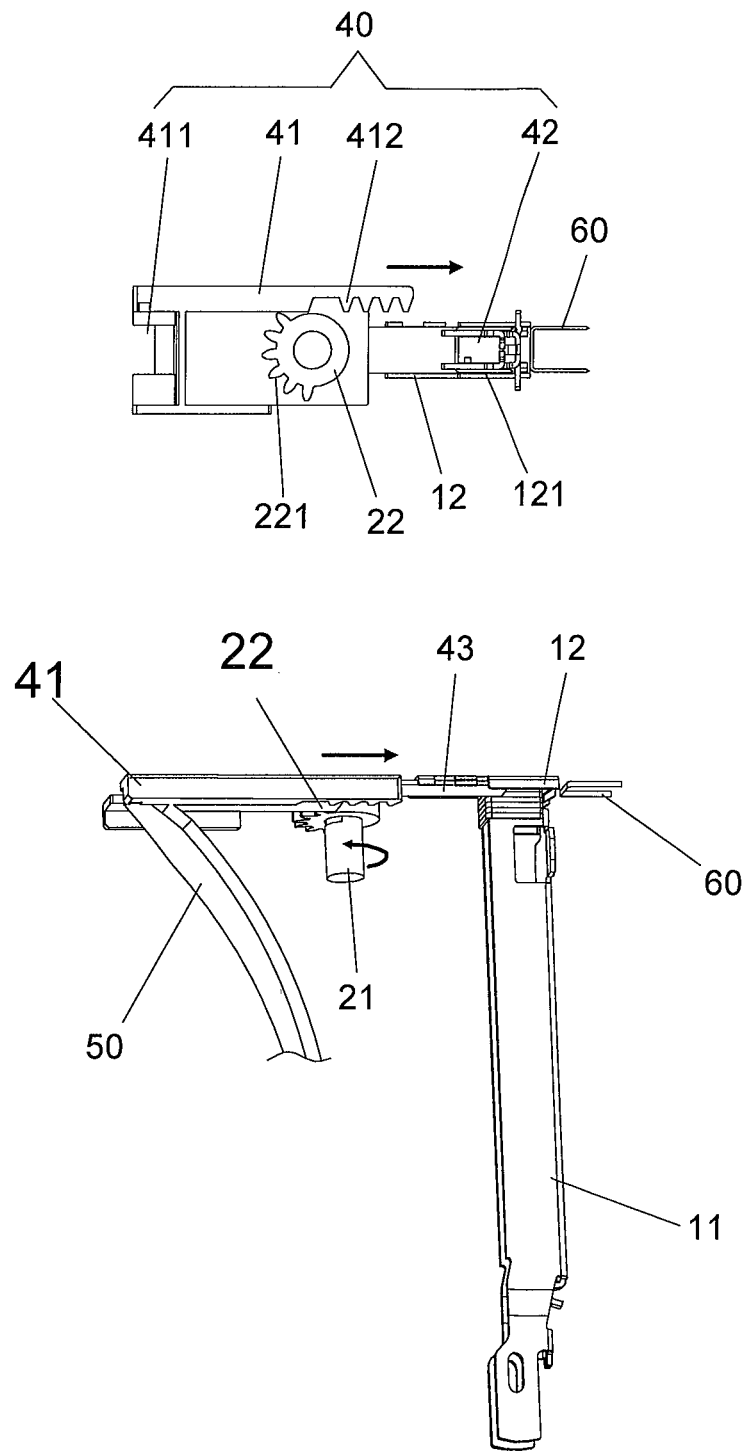
FIG. 7 shows that the teeth of the driving gear are disengaged from the rack, and the slide together with the push plate move toward right.
Figure 8:
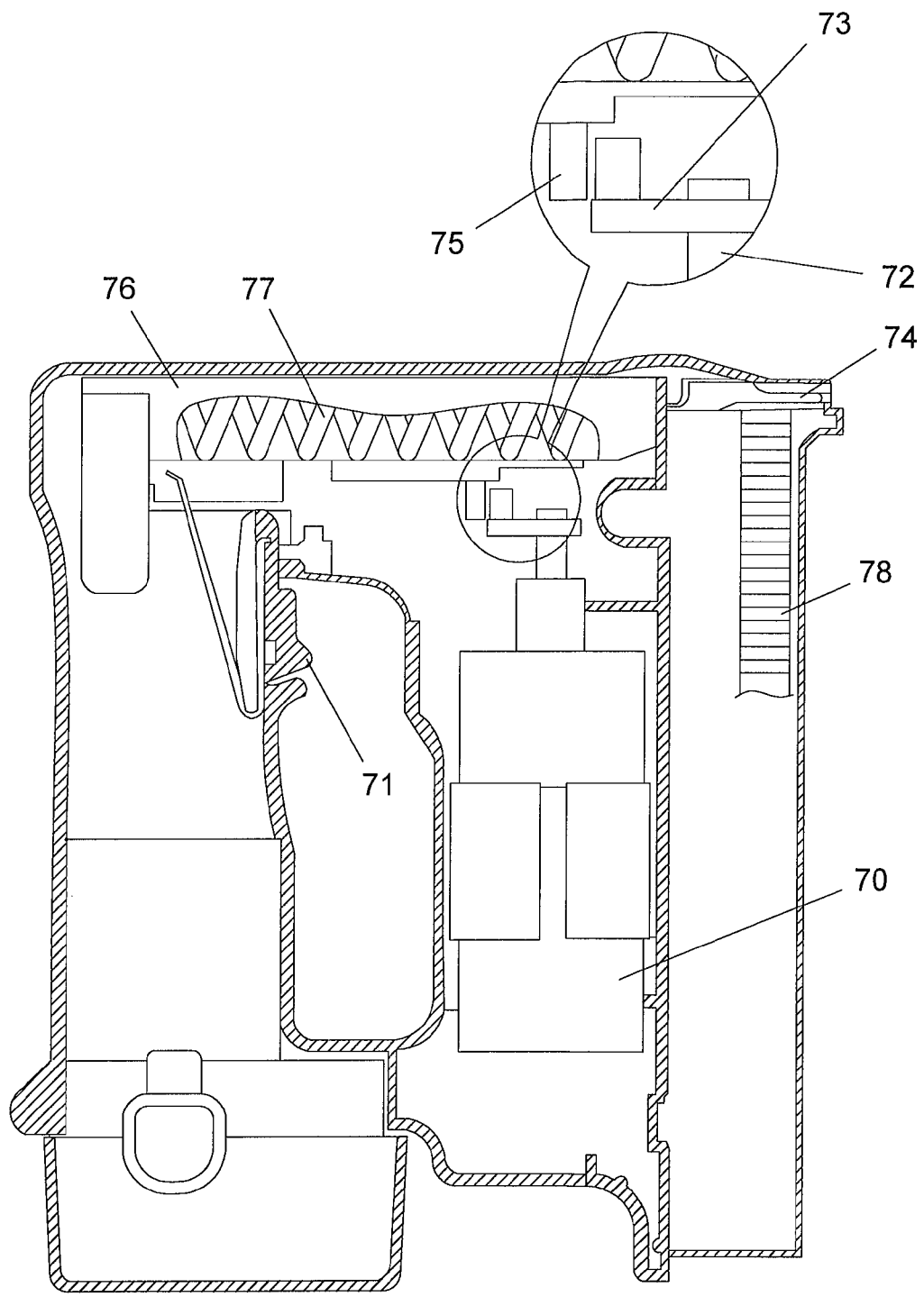
FIG. 8 shows the conventional staple push unit of a tacker.
Figure 9:
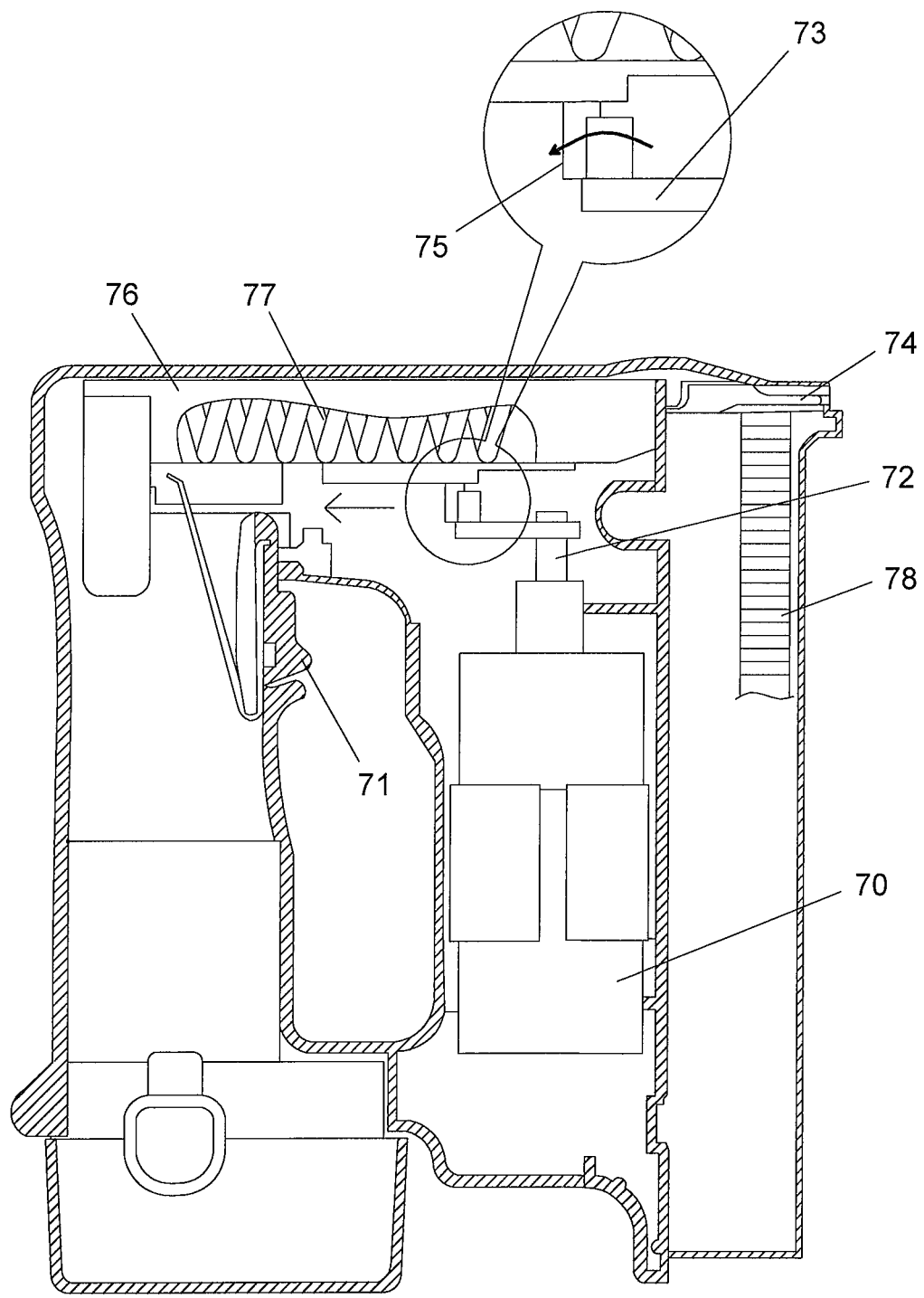
FIGS. 9 and 10 show the actions that the conventional staple push unit is in operation to eject a staple.
Figure 10:
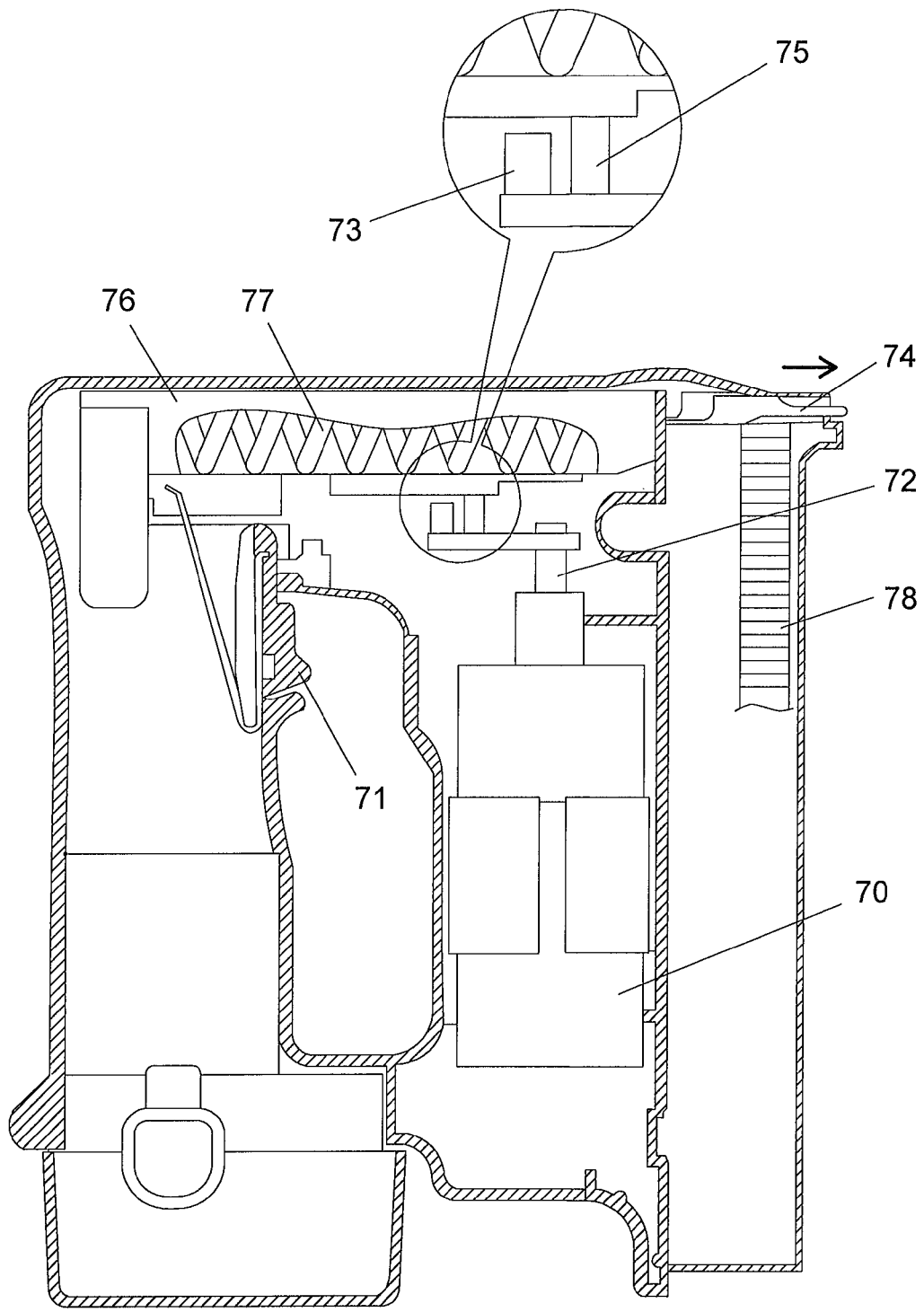

As shown in FIGS. 1, 2, 4 to 6, when the user pulls the trigger 30, the motor 20 is activated and the driving gear 22 is rotated by the output shaft 21 of the motor 20. The driving gear 22 drives the rack 412 to move the slide 41 away from the staple outlet of the tacker 10. The spring board 50 is bent with movement of the slide 41 to store energy as shown in FIG. 5. It is noted that in this embodiment, there is only six teeth 221 which are located only a portion of the outer periphery of the driving gear 22, and the rack 412 includes only four teeth, so that when the driving gear 22 is rotated to an angle, the teeth 221 of the driving gear 22 are disengaged from the rack 412 as shown in FIGS. 6 and 7, the spring board 50 bounces back and drives the slide and the push plate 42 toward the staple outlet of the tacker 10 to eject a staple out from the staple outlet.

There are no teeth on the driving gear 22 to be engaged with the rack 412 of the slide 41 after the teeth 221 are disengaged from the rack 412, so that the driving gear 22 will be rotated until the teeth 221 are engaged from the rack 412 again.

The teeth 221 of the driving gear 22 directly drive the rack 412 of the slide 41 to activate the push plate 42 to eject the staples, the transmission between the teeth 221 of the driving gear 22 and the rack 412 of the slide 41 is stable and precise.

The spring board 50 is directly engaged with the notch 411 of the slide 41, and the spring board 50 directly pushes the slide 41 and the push plate 42 to precisely eject the staples 60. The slide 41 and the push plate 42 are directly pushed by the spring board 50, the ejection of the staples 60 is precisely proceeded without delay.

While we have shown and described the embodiment in accordance with the present invention, it should be clear to those skilled in the art that further embodiments may be made without departing from the scope of the present invention.

What is claimed is:

1. A staples push unit of a tacker, comprising:
a magazine connected to a front end of the tacker so as to receive staples therein, a slot defined in the tacker, a guide plate located in the tacker and located at a staple outlet of the tacker;
a motor located in the tacker and having an output shaft, a driving gear connected to the output shaft and having teeth defined in an outer periphery thereof;
a trigger electrically connected to the motor;
a push unit located in the slot and having a slide and a push plate which is connected to a first end of the slide, the slide having a notch defined in a second end thereof, the slide having a rack formed at a side thereof, the rack engaged with the teeth of the driving gear, the push plate located within the guide plate and guided by the guide plate;
a spring board located in the tacker and having an end engaged with the notch of the slide, and
the driving gear driving the rack to move the slide away from the staple outlet of the tacker, the spring board being bent with movement of the slide, when the teeth of the driving gear are disengaged from the rack, the spring board bounces back and drives the slide and the push plate toward the staple outlet of the tacker to eject a staple out from the staple outlet.

2. The staples push unit of a tacker as claimed in claim 1, wherein the guide plate is located above an opening of the magazine.

3. The staples push unit of a tacker as claimed in claim 2, wherein the guide plate has two sidewalls between which a guide path is defined, the push plate is movably located in the guide path.

4. The staples push unit of a tacker as claimed in claim 1, wherein the rack on the slide is a straight rack and movable in the slot.

5. The staples push unit of a tacker as claimed in claim 1, wherein the teeth are defined in a portion of the outer periphery of the driving gear.

6. The staples push unit of a tacker as claimed in claim 1, wherein a spring is located in the trigger.

7. The staples push unit of a tacker as claimed in claim 1, wherein the push plate is connected to the slide by a pin.

* * * * *